United States Patent
Halsne et al.

(10) Patent No.: US 8,985,326 B2
(45) Date of Patent: Mar. 24, 2015

(54) CARRYING CASE FOR DEFIBRILLATOR WITH INTEGRATED BUTTON TESTER

(75) Inventors: Eric Halsne, Seattle, WA (US); Zebrick Roach, Seattle, WA (US); Kurt Vincent Fischer, Edmonds, WA (US); Daniel J. Powers, Issaquah, WA (US); Dennis E. Ochs, Bellevue, WA (US); Hans Patrick Griesser, Bainbridge Island, WA (US); Jacco Christof Eerden, Eindhoven (NL); Christian James Richard, Shoreline, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/882,537

(22) PCT Filed: Nov. 10, 2011

(86) PCT No.: PCT/IB2011/055011
§ 371 (c)(1),
(2), (4) Date: Apr. 30, 2013

(87) PCT Pub. No.: WO2012/063215
PCT Pub. Date: May 18, 2012

(65) Prior Publication Data
US 2013/0213840 A1    Aug. 22, 2013

Related U.S. Application Data

(60) Provisional application No. 61/412,520, filed on Nov. 11, 2010.

(51) Int. Cl.
*A61N 1/39*    (2006.01)

(52) U.S. Cl.
CPC .................................... *A61N 1/3968* (2013.01)
USPC ......................................... 206/363; 206/438

(58) Field of Classification Search
USPC ......................................... 206/438, 363, 305
See application file for complete search history.

(56) References Cited

U.S. PATENT DOCUMENTS

| | | | | |
|---|---|---|---|---|
| 3,787,767 | A | * | 1/1974 | Hammer et al. ............... 324/142 |
| 5,800,460 | A | * | 9/1998 | Powers et al. ...................... 607/5 |
| 5,897,576 | A | * | 4/1999 | Olson et al. ........................ 607/5 |
| 6,152,303 | A | | 11/2000 | Ducote et al. |
| 6,327,497 | B1 | * | 12/2001 | Kirchgeorg et al. .............. 607/3 |
| 6,422,669 | B1 | | 7/2002 | Salvatori et al. |
| 7,848,805 | B2 | * | 12/2010 | Ochs et al. ......................... 607/5 |
| 8,005,552 | B2 | * | 8/2011 | Covey et al. .................. 607/142 |
| 2003/0167075 | A1 | * | 9/2003 | Fincke ............................... 607/8 |
| 2011/0257695 | A1 | | 10/2011 | Jonsen et al. |

FOREIGN PATENT DOCUMENTS

| | | |
|---|---|---|
| CN | 2067145 U | 12/1990 |
| CN | 101218668 A | 9/2009 |
| DE | 202005008828 U1 | 10/2005 |
| EP | 1683544 A1 | 7/2006 |

* cited by examiner

*Primary Examiner* — Steven A. Reynolds

(57) ABSTRACT

A substantially rigid defibrillator carrying case having a hinged side, a latch disposed on a latch side opposite the hinged side, and a handle disposed on a handle side disposed between the hinged side and the latch side. The carrying case is constructed without protrusions and with a rigid handle, which combine to allow easy removal and deployment of the contents from a vehicle storage location to a cardiac arrest patient. The carrying case integrates a actuator to periodically test the operation of the defibrillator push buttons.

6 Claims, 9 Drawing Sheets

CARRYING CASE FOR DEFIBRILLATOR WITH INTEGRATED BUTTON TESTER

BACKGROUND OF THE INVENTION

This invention relates to defibrillators for cardiac resuscitation and, in particular, to carrying cases for defibrillators.

Cardiac arrest is a life-threatening medical condition in which the patient's heart fails to provide blood flow to support life. A defibrillator can be used to deliver defibrillating shocks to a patient suffering from cardiac arrest. The defibrillator resolves this condition by delivering a high-voltage impulse to the heart in order to restore normal rhythm and contractile function in patients who are experiencing arrhythmia such as VF (ventricular fibrillation) or VT (ventricular tachycardia) that is not accompanied by spontaneous circulation. One type of defibrillator, the automated external defibrillator (AED), differs from manual defibrillators in that the AED can automatically analyze the electrocardiogram (ECG) rhythm to determine if defibrillation is necessary. The defibrillator analyzes the ECG signal for signs of arrhythmia. If VF is detected, the defibrillator signals the rescuer that a shock is advised. After the detection of VF or other shockable rhythm, the rescuer presses a shock button on the defibrillator to deliver a defibrillation pulse to resuscitate the patient.

Defibrillation must be delivered very soon after the onset of cardiac arrest in order to be effective. It is estimated that the chance of survival falls by 10% for every minute of delay to defibrillation beyond four minutes after cardiac arrest. Hence, AEDs are designed to be used by first responders, such as firefighters, police, or lay bystanders, who are the most likely to arrive at the patient's side first. Once an AED is brought to the patient, the rescuer must deploy and use it quickly. Such quick use is often challenging, because the rescuer may be unfamiliar with the AED's setup and operation.

External defibrillators act through electrode pads applied across the chest of the patient. The electrodes adhesively attach to the patient and are used both to acquire an ECG signal from the patient's heart and to apply the defibrillating shock. AED electrodes commonly are formed by locating a foil or metalized electrode between a flexible nonconductive backing and a conductive adhesive gel. The conductive adhesive attaches the electrode securely to the patient. Gels, however, will dry out (desiccate) over time and have a finite shelf life. A typical shelf life for an electrode with gel adhesive is about two years, after which the electrodes must be replaced. Some AEDs use electrodes which are simply replaced when the safe shelf life period has expired. Other AEDs have an internal self-test circuit which periodically tests the electrodes and detects desiccation by an impedance change. For self-test electrodes the electrodes are electrically connected to each other to form a continuous closed loop circuit that is tested. The closed loop circuit is broken when the electrode pads are deployed for use.

In the case of both self-tested electrodes and non-self-tested electrodes, it is typical that the electrodes will be connected to the AED while stored prior to use so that the rescuer does not need to connect them during the emergency; they are already pre-connected and ready for use. Pre-connected electrodes are commonly stored inside a protective container that is the same or co-located as a carrying case for an AED, so that the electrodes are protected from puncture or damage during storage, yet are instantly available for deployment when the AED case is opened.

Some AEDs also include accessories which aid in the administration of cardiopulmonary resuscitation (CPR) during the rescue. For example, the QCPR meter, sold by Philips Electronics North America, is a puck-like sensor which is placed on the patient's chest, and over which manual CPR compressions are applied. The QCPR meter contains force and motion sensors which provide an indication of the quality of the CPR applied via a signal cable to a defibrillator.

The AED may also include a pediatric mode accessory that, when applied to the AED, causes the AED to analyze and provide therapy appropriate to pediatric patients. The pediatric mode accessory may be shaped like a key which is inserted into an AED socket for use. When not in use, the key is stored elsewhere in the carrying case.

In addition, AED carrying cases may also include a fast response kit, which contains such rescue items as sterile gloves, scissors for cutting clothing away from a patient's chest, a razor for shaving excess chest hair, and a rescue breathing shield. A spare battery for the AED, spare electrode set, and written user guide may also be included in the carrying case.

Prior art AED carrying cases suffer a number of problems. First, the cover and handle on some prior art carrying cases hamper the application of therapy to the patient. Handles typically consist of strapping, which easily tangles with other gear stored or carried by the rescuer, delaying deployment. Handles may also be arranged to cover the AED cover latch, which may impede the ability of a glove-wearing rescuer to open the cover. Carrying case lids, when open, may be disposed such that they can easily be stepped on and broken by the rescuer, kicked shut by the rescuer, or otherwise impede access to the patient lying alongside. All of these characteristics serve to delay therapy.

Next, some carrying cases are arranged such that important contents are not visible at the time of deployment. A fast response kit, for example, may be stored in a separate pocket from the AED. A rescuer using such a carrying case may be delayed in finding and/or deploying the kit during rescue.

Prior art carrying case latches may be insufficiently robust to prevent inadvertent opening when the case is dropped, thus exposing the contents to damage or otherwise delaying the rescue. Some latches are simply Velcro closures.

Prior art carrying cases may be ill-disposed for ease of cleaning and checking of the contents, presenting risk of cross-contamination and malfunction during the next rescue. For example, some prior art AED carrying cases have no internal trays that are removable for cleaning. None have any means of testing internal components, such as a CPR guidance device or the defibrillator push buttons, prior to the rescue. If the AED contained in the carrying case has a ready-for-use indicator on its face, the case window may be too small to allow easy viewing of the indicator.

BRIEF SUMMARY OF THE INVENTION

In accordance with the principles of the present invention, a carrying case for a defibrillator is described which enables more rapid deployment and use during a cardiac rescue. Improvements include a relatively stiff and curved handle that is disposed at a 90 degree angle to both of the case hinge and the case latch. The shape and stiffness of the handle act to prevent entanglement with other gear during storage and removal. The orientation of the handle allows for use of the handle during rescue while simultaneously avoiding interference with latch actuation and lid opening.

In accordance with another aspect of the invention, a carrying case is described having a relatively rigid protective base and lid shell, connected by a double articulated hinge. The hinge is disposed such that, when in the open position, the carrying case base and lid are essentially co-planar. The case cannot be inadvertently closed while in the open position, and by the nature of the hinge, resists damage if stepped on while in the open position. A novel case seal between lid and base is described that prevents damage to any AED electrode or CPR meter wires that protrude from the case when the lid is inadvertently closed. Thus, the invention provides increased robustness and ease of use during rescue.

In accordance with yet another aspect of the invention, a carrying case is described with an improved arrangement of contents. All material required for cardiac rescue is immediately visible once the carrying case is opened. Provision for compact storage of electrode and CPR meter wire bundles is provided. Spares and other non-essential material are hidden, thus minimizing confusion during rescue. An automatic turn-on feature in the carrying case can optionally activate the defibrillator when the case lid is opened. An improved seal between lid and base is described which prevents pinching of wires if the lid is inadvertently closed during use.

In accordance with yet another aspect of the invention, a carrying case is described having improved ability to check and clean the cardiac rescue contents. The case may comprise an internal CPR meter holding bracket, a CPR meter test fixture, a light pipe for wider-angle viewing of a ready-indicator on an internal AED, a defibrillator button tester and/or trays removable for cleaning and/or replacement.

In accordance with yet another aspect of the invention, a carrying case with an improved closure latch is described. The latch is a rigid and hinged mechanism which consists of a spur and catch assembly that is held in positive engagement by a second hook and lock assembly. The latch may be opened with one hand and in one motion, and can be closed and locked by simply pressing the mechanism shut. When closed and locked the latch pull is flush to the carrying case for ease of deployment from the case storage location.

BRIEF DESCRIPTION OF THE SEVERAL VIEWS OF DRAWINGS

DETAILED DESCRIPTION OF THE INVENTION

Figure 1A:
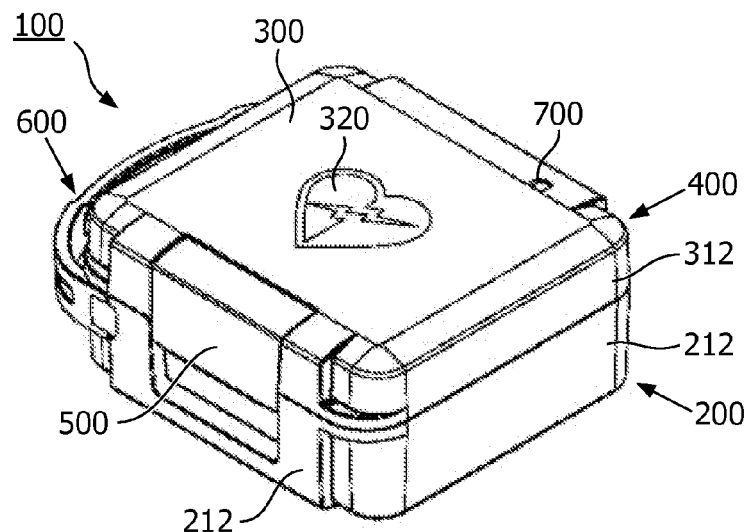
FIGS. 1a and 1b illustrate a defibrillator carrying case constructed in accordance with the principles of the present invention, in the closed and open positions respectively.

Referring first to FIG. 1a, a defibrillator carrying case 100 according to the principles of the present invention is shown in the closed position. The carrying case 100 is sized to contain and protect components needed for a cardiac arrest rescue, such as an AED with pre-connected electrodes, a CPR meter, a fast response kit, and associated spares, not shown. The carrying case 100 protective surfaces consist primarily of two case halves; a base 200 and a lid 300. Base 200 and lid 300 are fabricated of a lightweight and substantially rigid structural material, such as plastic, metal or a composite material. The material resists puncture, abrasion, water ingress and shock to protect the interior contents. In a preferred embodiment, base 200 and lid 300 are constructed of molded structural foam polypropylene or like material. Base 200 comprises four base walls 212 and a base bottom 214, together forming a base interior region 210. Similarly, lid 300 comprises four lid walls 312 and a lid top 314, together forming a lid interior region 310.

As shown in FIG. 1a, a hinge 400 connects the carrying case halves together across one wall base wall 212 of base 200 and one lid wall 312 of lid 300. Latch assembly 500 is disposed across base 200 and lid 300 across a different base wall 212 and lid wall 312 opposite the hinge 400 to securely hold the carrying case halves in the closed position. A rigid or semi-rigid and arcuate handle 600 is attached at both ends across a carrying case side adjacent to both the carrying case 100 hinged side and the latched side. Each of the hinge 400, latch assembly 500, and handle 600 are disposed such that all surfaces contacting the carrying case are flush with the carrying case surfaces when the case is closed.

Figure 1B:
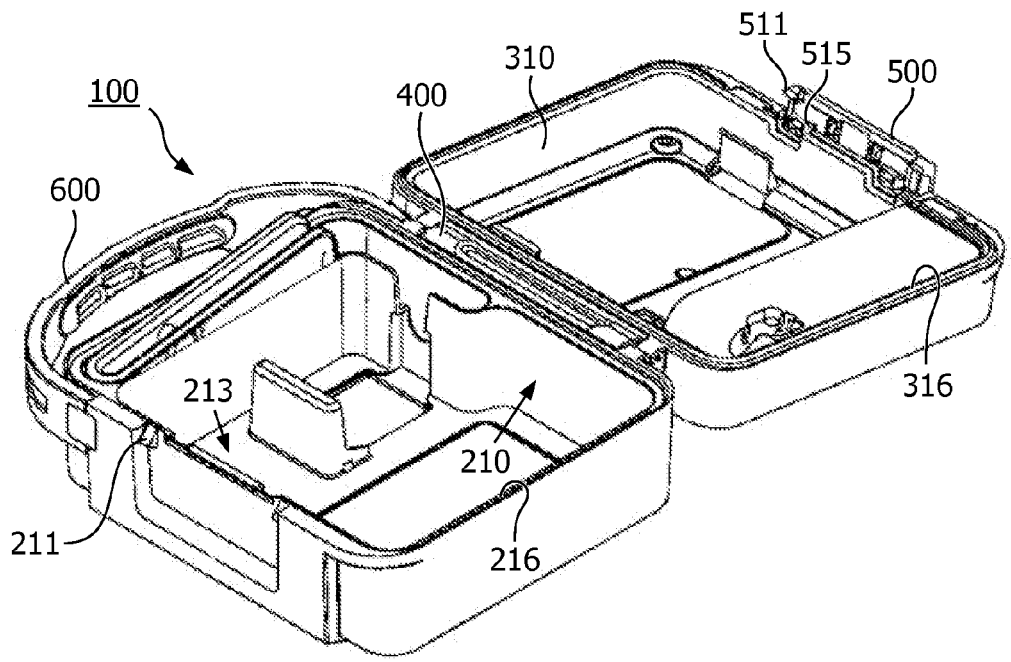

FIG. 1b illustrates the carrying case 100 in the open position. The base walls 212 and base bottom 214 together form a base interior region base interior region 210. Similarly, the lid walls 312 and lid top 314 together form a lid interior region 310. A removable base tray 800 may be nested inside base interior region base interior region 210, and a removable lid tray 820 may be nested inside lid interior region 310.

Lid 300 or lid tray 820 may also comprise a case opening indicator 720, preferably a magnet, which is affixed to the lid. So located, indicator 720 overlays a corresponding case opening sensor inside portable defibrillator 110 only when carrying case 100 is closed. Portable defibrillator 110 senses an open lid by the absence of indicator 720, and thus turns itself on. It is noted that a feature that automatically turns portable defibrillator 110 off upon the shutting of lid 300 should be avoided, in order to prevent unnecessary delay and confusion involved with an inadvertent lid closure, and unintended defibrillator shutdown, during rescue.

Additional detail of the interaction between latch assembly 500, base 200 and lid 300 is shown in FIG. 1b, wherein base 200 is disposed with a case beveled catch 211 and base lock 213 which correspond to a beveled spur 511 and latch hook 515 respectively on latch assembly 500. FIG. 1b also illustrates an anti-pinch case sealing mechanism, comprising opposing base seal edge 216 and lid seal edge 316, formed along the exposed edges of base walls 212 and lid walls 312 respectively.

The relatively rigid nature of the handle and the flush-mount design of its attachment to the carrying case 100 provide a smooth carrying case 100 profile shape of the case.

Because carrying case 100 is typically stored in rescue vehicle compartments with other gear, the smooth overall profile and lack of mount protrusions allow the rescuer to grasp and pull the carrying case 100 out of the compartment without fouling other gear. Similarly, the latch mechanism and hinge are disposed to be flush to the carrying case 100 when closed and will not catch on other material when the carrying case 100 is pulled from the compartment. These features save precious seconds and reduce time to defibrillation.

The particular placement of the rigid handle 600, latch assembly 500, and hinge 400 on separate sides of the carrying case 100 solves several problems unaddressed by the prior art. By locating the handle away from the latch, the access to and operability of the latch is improved, especially for heavily gloved responders. By locating the handle away from the hinge, the handle is available for use in repositioning the carrying case 100 even when in the open position.

Figures 8A, 8B:
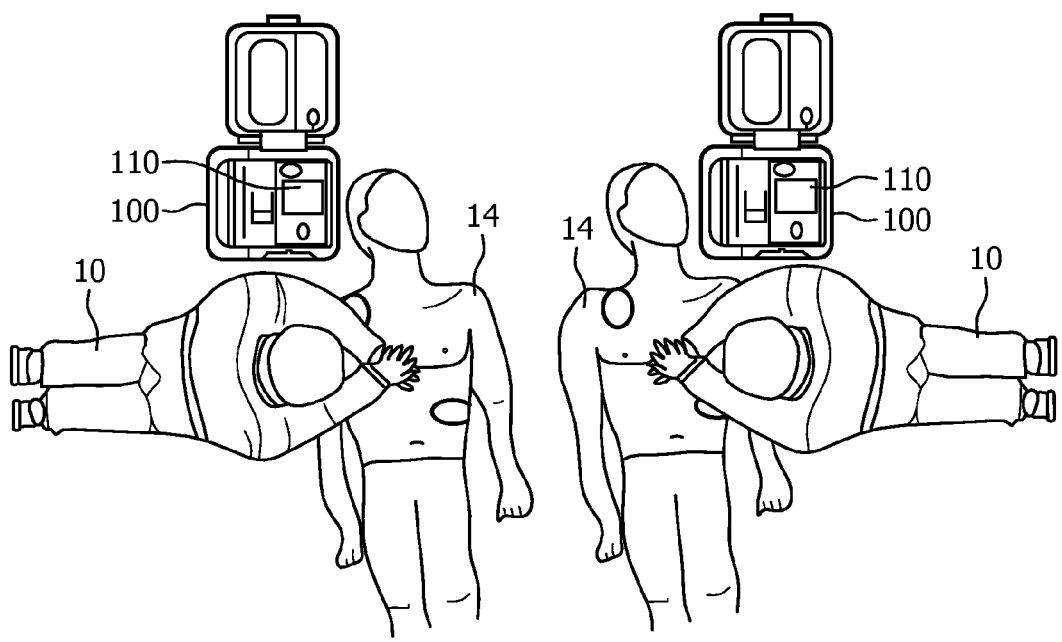
FIG. 8 illustrates the carrying case in use during a cardiac rescue.

The present invention also improves the utility of the carrying case 100 when it is deployed next to a cardiac arrest patient. FIG. 8 illustrates. A rescuer 10 typically takes position alongside the prone cardiac arrest patient 14 in order to provide CPR and monitoring of the patient. A portable defibrillator 110 stored within carrying case 100 is deployed on the patient to provide electrotherapy. Portable defibrillator 110 must be oriented such that its display can be easily viewed by the rescuer, and so is typically placed alongside the patient's head such that the bottom of the portable defibrillator 110 display is toward the rescuer. In this position, carrying case 100 offers the advantage that in the open position, the orientation of the hinge at the top of the portable defibrillator 110 display results in lid 300 always extending away from the rescuer and also cannot be opened to lie on the patient's face. It can be seen in FIG. 8 that this advantage applies even when the rescuer deploys the portable defibrillator 110 on the other side of the patient.

In the open position, carrying case 100 is more stable and robust than prior art carrying cases. As shown in FIG. 1b, base 200 and lid 300 are substantially co-planar in the open position. The hinge 400 design, described in more detail below, allows lid 300 to rotate to 180 degrees and greater, and also allows for a slight and beneficial lateral movement from base 200. Thus, when open, the top surface of lid 300 contacts the same surface as the bottom of base 200. This provides a more stable platform for the rescue contents. The lid 300 in this position cannot inadvertently be kicked shut. In addition, the lateral movement feature provides enhanced resistance to damage because, if stepped on, hinge 400 will merely self-adjust the orientation of base 200 to lid 300 instead of breaking.

The height of the base wall 212 and the lid wall 312 need not be equal to achieve the aforedescribed advantages. However, the design of hinge 400 can be somewhat simplified if the base wall 212, lid wall 312 are equal, because the top of lid 300 and the bottom of base 200 will completely contact the resting surface when carrying case 100 is open.

Figure 7:
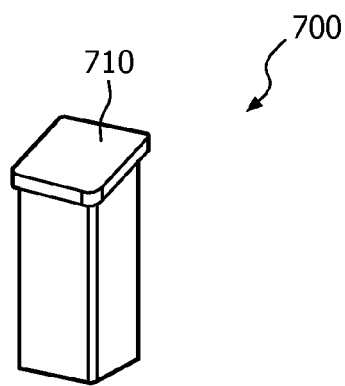
FIG. 7 is a detail view of an exemplary carrying case light pipe for conveying the ready indication light signal from an internal stored defibrillator to the exterior of the case.

Several other advantages are offered by the carrying case 100 exterior features. The design of carrying case 100 promotes ease of maintenance. Light pipe 700 conveys a ready status light signal from an interior mounted AED to the carrying case 100 exterior. Light pipe 700 includes a means for diffusing the transmitted ready status light 111 signal, thereby making the indicator visible over a much wider angle of view. FIG. 7 illustrates one embodiment of light pipe 700, wherein the means for diffusing comprises etching or sandblasting an exterior surface 710 of light pipe 700. The other surfaces of light pipe 700, preferably constructed of clear acrylic or like material, are polished. The etching serves to diffuse the transmitted light signal over a wide angle, such that visual checks of the internal AED can be completed without opening carrying case 100.

Removable base tray 800 and lid tray 820 also promote ease of maintenance in the carrying case 100. Cardiac rescues typically involve bodily fluids and other contaminants, which must be removed from equipment after each use. Base tray 800 and lid tray 820 can easily be removed to clean the interior surfaces of carrying case 100. Replaceability of base tray 800 and lid tray 820 also offers other advantages, such as replacement of a damaged tray, reconfiguration if a different internal equipment configuration is needed, or if there is no time for cleaning prior to the next cardiac rescue.

Figure 2A:
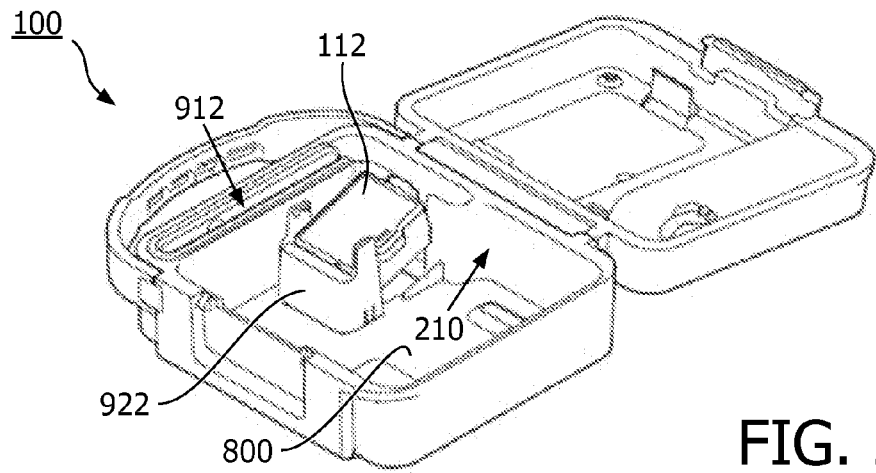
FIGS. 2a and 2b illustrate a preferred carrying case storage configuration for non-emergency spare battery and electrodes, respectively, which are hidden from sight during emergency use.
Figure 2B:
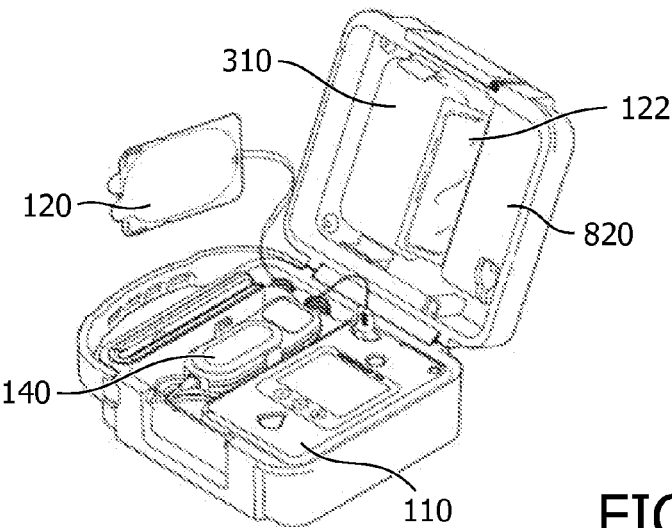
Figure 2C:
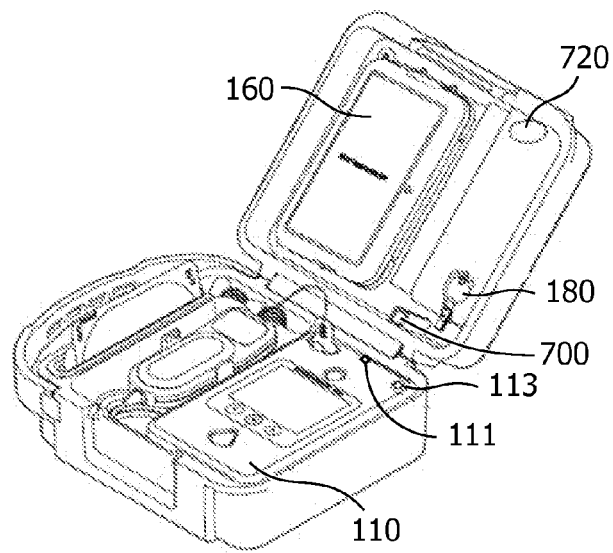
FIG. 2c illustrates a preferred embodiment of the carrying case interior arrangement.

FIGS. 2a, 2b and 2c illustrate a preferred embodiment of the arrangement of carrying case 100 interior contents. Carrying case 100 is generally configured such that when the lid 300 is opened, the rescue equipment that is most immediately needed is visible to the user and ready to use. Equipment that is not immediately needed is hidden from view in order to reduce clutter and confusion. FIG. 2a illustrates an embodiment of carrying case 100 wherein a spare battery 112, normally not needed at the beginning of a cardiac rescue, is stowed behind a CPR meter storage bracket 922 and subsequently hidden from view by a stored CPR meter 140. FIG. 2a also shows an electrode storage slot 912 that is installed at the handle-end of carrying case 100 for containing a pre-connected set of electrodes 120. Electrode storage slot 912 secures electrodes 120 in an instantly-visible and accessible manner. Co-pending and co-assigned U.S. application Ser. No. 12/827,142 entitled "PINCH CASE FOR DEFIBRILLATOR ELECTRODE PADS AND RELEASE LINER", fully incorporated herein, describes a preferred embodiment of electrode storage slot 912 and electrodes 120 which can be employed in carrying case 100.

Both of electrode storage slot 912 and CPR meter storage bracket 922 are shown in FIG. 2a as installed in base tray 800 within base interior region 210. However, it is understood that either fixture may also be installed directly into base interior region 210 without the need for base tray 800 at all.

FIG. 2b illustrates the relative arrangement of portable defibrillator 110, CPR meter 140 and electrodes 120 within base interior region 210. portable defibrillator 110 is disposed to the right side, CPR meter 140 disposed on CPR meter storage bracket 922 in the center, and electrodes 120 disposed in electrode storage slot 912. Each is instantly visible and accessible when portable defibrillator 110 is opened. In addition, electrodes 120 and CPR meter 140 are pre-connected to portable defibrillator 110, and connection wires stowed out of the way. Thus, the operator may begin deploying the equipment immediately upon opening the case.

FIG. 2b also shows a set of spare electrodes 122 stowed out of sight behind a panel formed in lid tray 820. It is understood that lid tray 820 may be integrated with and form part of lid interior region 310 instead of being a separate removable component.

Turning now to FIG. 2c, additional cardiac rescue components fast response kit 160 and pediatric mode key 180 are shown stowed for immediate deployment in lid interior region 310. Fast response kit 160 may be completely removable as a kit from carrying case 100 for opening elsewhere in the rescue. Pediatric mode key 180 may be press-fit into a similarly shaped indentation in lid tray 820, as shown, and/or may be connected to carrying case 100 via a retractable tether stowed behind the lid tray 820 panel. When portable defibrillator 110 is to be used on a pediatric patient, the operator simply inserts pediatric mode key 180 into a pediatric mode changing slot 113. Portable defibrillator 110 senses the insertion and changes into a pediatric mode of operation.

FIG. 2c also shows the disposition of light pipe 700 over ready status light 111. When lid 300 is shut, light pipe 700 overlays ready status light 111. Any indicator light signal on ready status light 111 is then transmitted through light pipe 700 to the exterior of portable defibrillator 110 for ease of viewing without having to open the case.

Figure 3A:
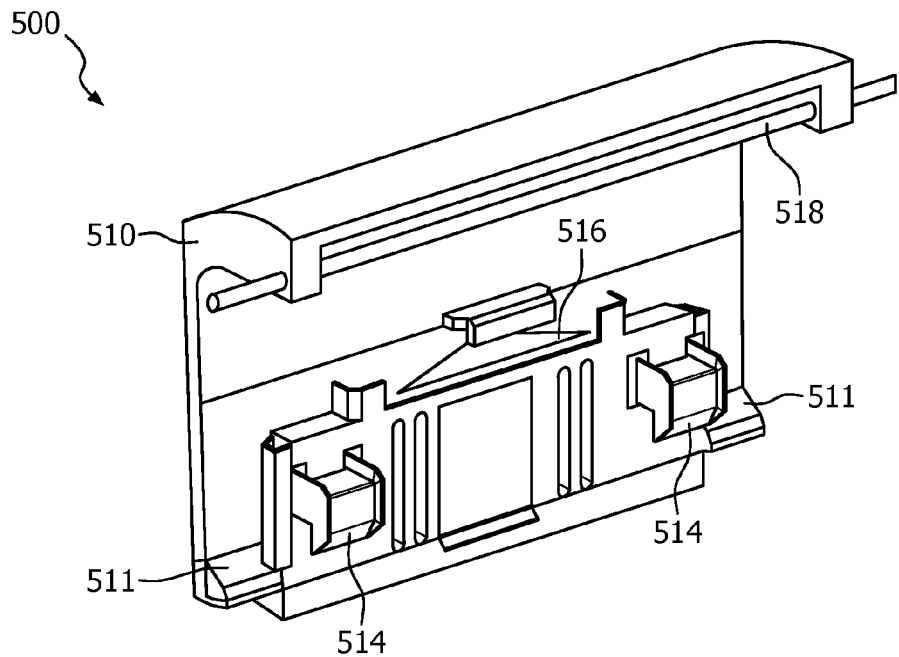
FIG. 3a is a detail view of an exemplary carrying case latch assembly.

Referring to FIG. 3a, an embodiment of a latch assembly 500 for carrying case 100 is illustrated. Latch assembly 500 comprises a relatively flat latch pull 510 having a beveled spur 511 for engaging a corresponding beveled catch 211 disposed on base wall 212. Latch assembly 500 also comprises a latch plate 514 which slidably translates relative to latch pull 510 against latch spring 516. A portion of latch plate 514 extending below latch pull 510 serves as a manual operating surface to compress the latch plate 514 against latch spring 516. Latch pull 510 is preferably constructed of a rigid and strong material, such as metal or plastic, that can withstand impact and operational abuse.

Figures 3B, 3C:
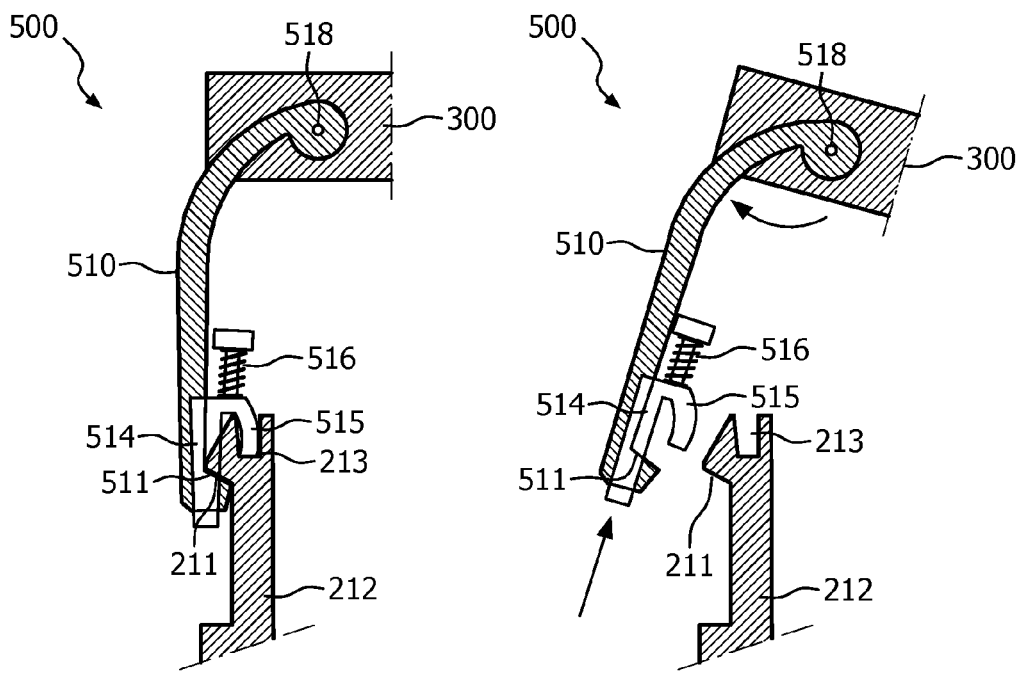
FIGS. 3b and 3c illustrate the latch assembly opening action.

FIG. 3b illustrates the geometry and operation of latch assembly 500 with carrying case 100 closed. In the closed position, the beveled spur 511 and beveled catch 211 are held in compressive contact primarily through the holding tension of latch assembly 500 relative to base 200 and lid 300. As shown in FIG. 3a, latch hook 515 further engages base lock 213 formed in base wall 212 to securely hold the beveled spur 511 against beveled catch 211. The combination of beveled spur 511 and latch hook 515 thus prevent the latch from popping open even if the case is dropped. FIG. 3b also shows a preferred configuration of base wall 212, whose exterior surface is substantially co-planar with the latch pull 510 exterior surface, except for the indented operating area just under beveled spur 511.

FIG. 3c illustrates the operation of latch assembly 500 to open carrying case 100. The operator releases latch assembly 500 by pressing upward on latch plate 514 against latch spring 516, which in turn releases latch hook 515 from base lock 213. The beveled spur 511 and beveled catch 211 are suitably angled with respect to the base wall 212 surface, so that upon the release of latch hook 515, the operator can smoothly rotate latch assembly 500 about latch pin 518 and away from base wall 212 for opening. Thus, the opening operation can be accomplished with one hand and in one motion. Upon subsequent release of the latch plate 514, latch spring 516 returns latch plate 514 to its initial position which is ready for closing.

Further inspection of FIG. 3 also shows how latch assembly 500 is closed and locked. To latch carrying case 100 closed, the operator merely presses latch pull 510 about latch pin 518 until the angled interior surface of latch hook 515 and the upward-facing angled surface of beveled catch 211 are in contact. The operator firmly presses latch pull 510, thereby causing latch hook 515 to slide upward and along the contact surface, opposed by latch spring 516, until latch hook 515 engages into base lock 213. Alternatively, the operator may press upward and then release latch plate 514, while pressing latch pull 510, to cause latch hook 515 to engage base lock 213.

Figure 4A:
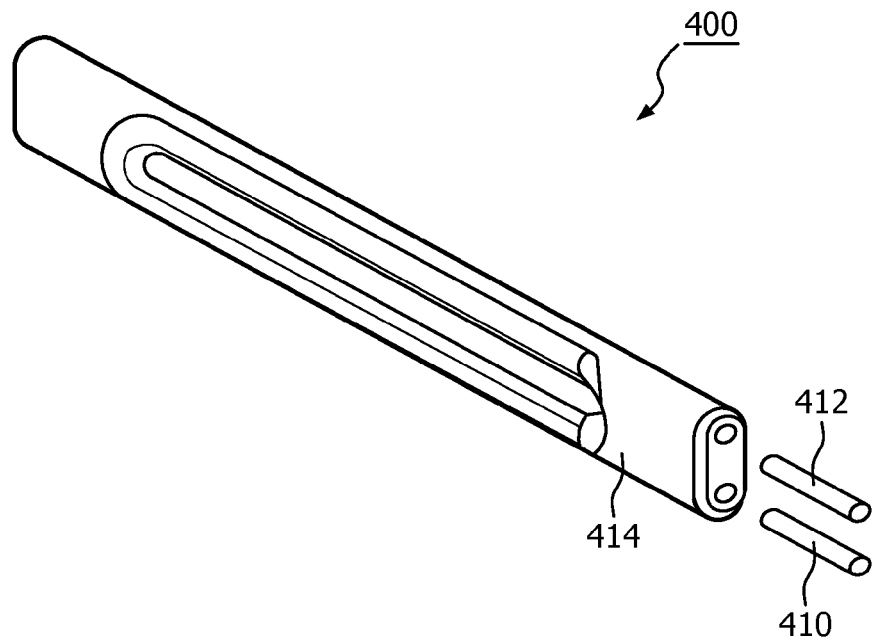
FIG. 4a is a perspective view of an exemplary carrying case hinge constructed in accordance with the principles of the present invention.

Referring to FIG. 4a, carrying case 100 preferably comprises a hinge 400, similar to a floating hinge, for hingably connecting lid 300 to base 200. Hinge 400 comprises an articulated body 414 which is interposed between lid 300 and base 200. Articulated body 414 is in turn connected to base 200 on each end by a bottom hinge pin 410, and also to lid 300 on each end by a top hinge pin 410. Articulated body 414 is constructed of a rigid material which can add strength to the structure when carrying case 100 is closed, and can also add structural strength to carrying case 100 when carrying case 100 is open. Articulated body 414 is preferably made of the same material as base 200 and lid 300. Bottom hinge pin 410 and top hinge pin 410 are of stainless steel or similar material.

Figure 4B:
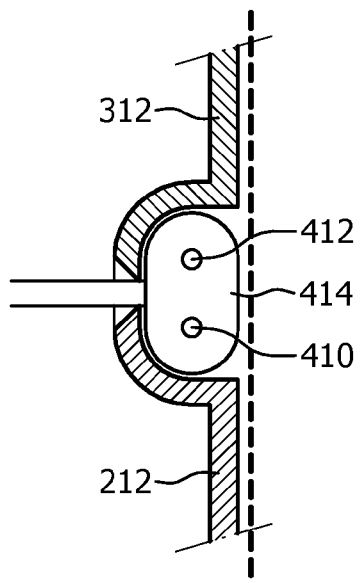
FIGS. 4b AND 4c illustrate the action of the hinge in concert with the carrying case halves.
Figure 4C:
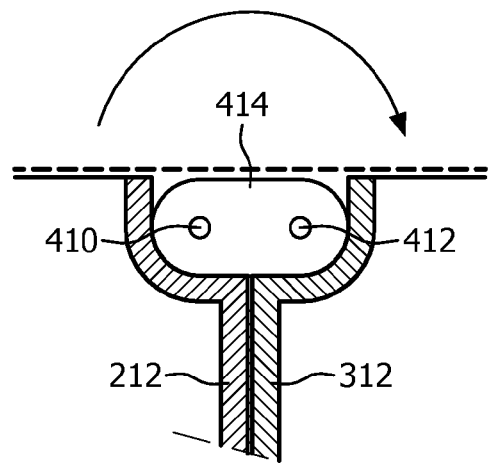

FIGS. 4b and 4c illustrate the operation of hinge 400 in the closed and open positions respectively. As illustrated in FIG. 4b, hinge 400 is disposed such that when carrying case 100 is closed, an articulated body 414 surface is flush to the surfaces of base wall 212 and 312. FIG. 4c shows carrying case 100 open. In the open position, both 312 and articulated body 414 are rotated from their closed position, such that an opposite articulated body 414 surface is flush to the open faces of base 200 and lid 300.

In addition to the advantages offered by the flush construction, hinge 400 provides structural strength and protection to the hinge area formed between base wall 212 and lid wall 312. In addition, the articulated nature of articulated body 414 allows a limited amount of translational shifting between base wall 212 and lid wall 312, such that the hinge area can absorb crushing forces, such as those incurred when being driven over or stepped upon, that may break other hinge designs. As can be seen from inspection of FIGS. 4b and 4c, hinge 400 does so by allowing crushing forces to be distributed over the rounded surfaces of base wall 212 and 312 which contact articulated body 414 instead of in the concentrated area of bottom hinge pin 410 and top hinge pin 410. In the open position, hinge 400 also allows the opposing surfaces of base wall 212 and 312 to counter crushing forces from above.

Figure 5:
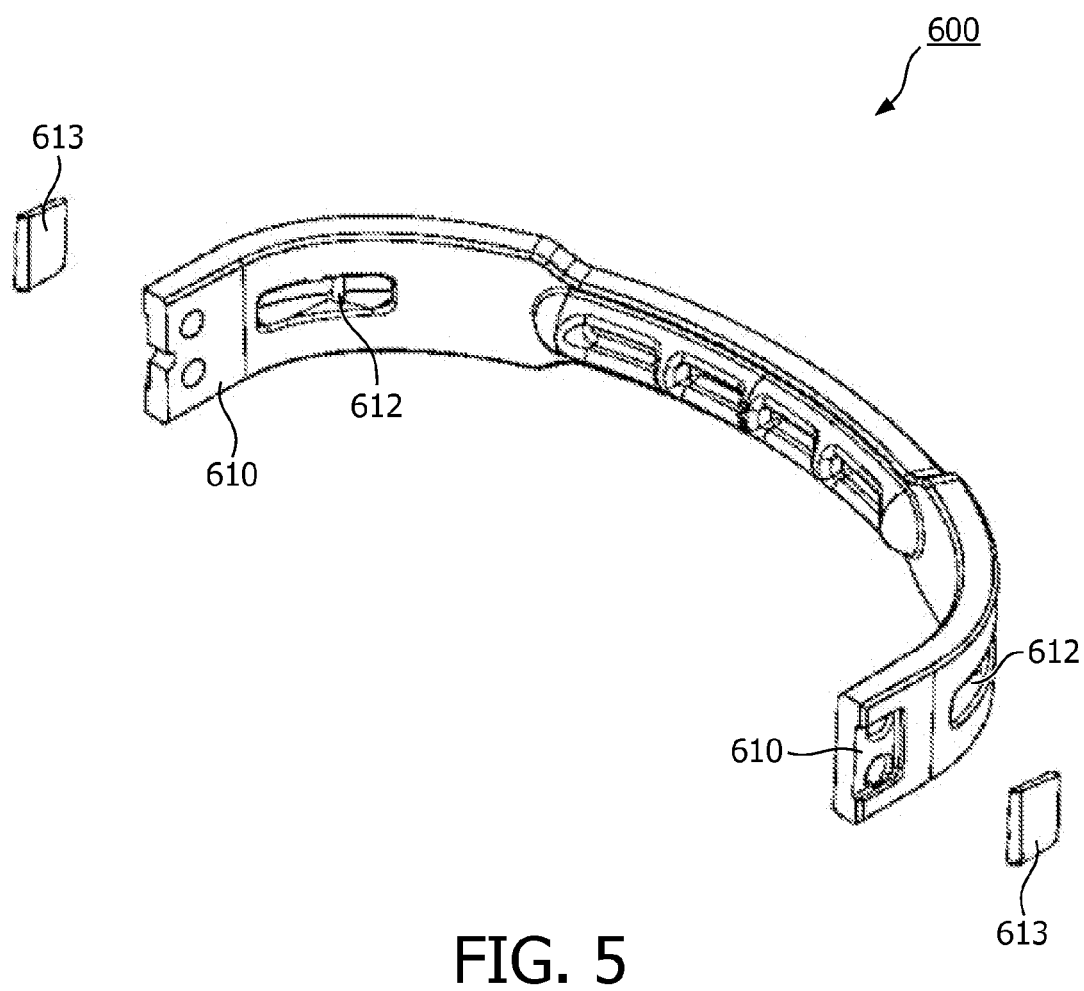
FIG. 5 is a detail view of a carrying case handle constructed in accordance with the principles of the present invention.

FIG. 5 illustrates a preferred embodiment of carrying case handle 600. The handle is comprised of a substantially rigid or semi-rigid material, like thermoplastic elastomer, which can flex but return to original shape. Handle 600 is preferably rounded or arcuate to allow for quick deployment without catching on other equipment. Shoulder strap pins 612 for mounting an optional shoulder strap, the strap not shown, may be molded into handle 600.

Handle 600 is attached to carrying case 100 as described previously and as seen in FIG. 1. FIG. 5 shows each end of handle 600 comprises a handle anchor 610, which is formed to be flush-mounted to opposite sides of carrying case 100 with known fasteners, not shown, such as screws or rivets. Flush-mounting may be completed by covering the fasteners with handle anchor cover plates 613. Once so disposed, the entire silhouette of carrying case 100 with handle 600, as viewed toward the lid top 314, presents a continuous smooth line which resists catching on adjacent material when carrying case 100 is pulled from its storage location.

Figure 6A:
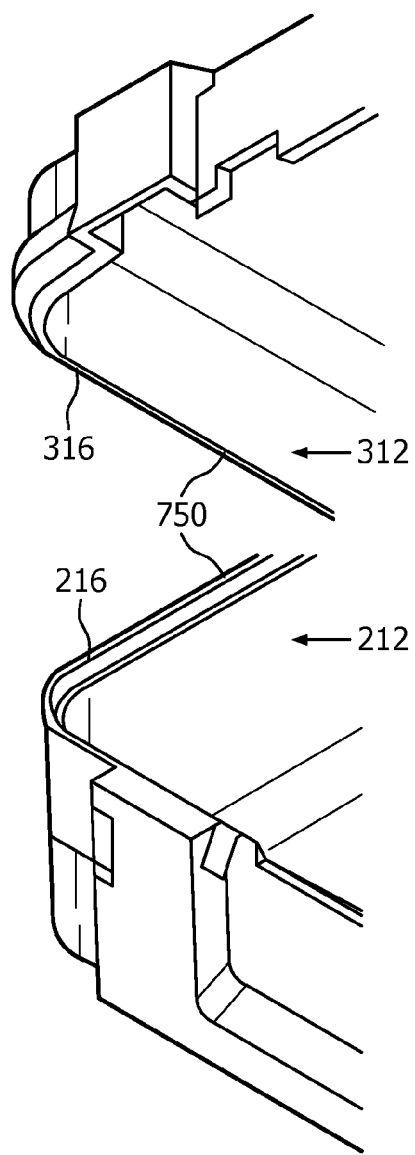
FIG. 6a is a detail view of an exemplary carrying case seal as disposed on the top and bottom carrying case halves.
Figure 6B:
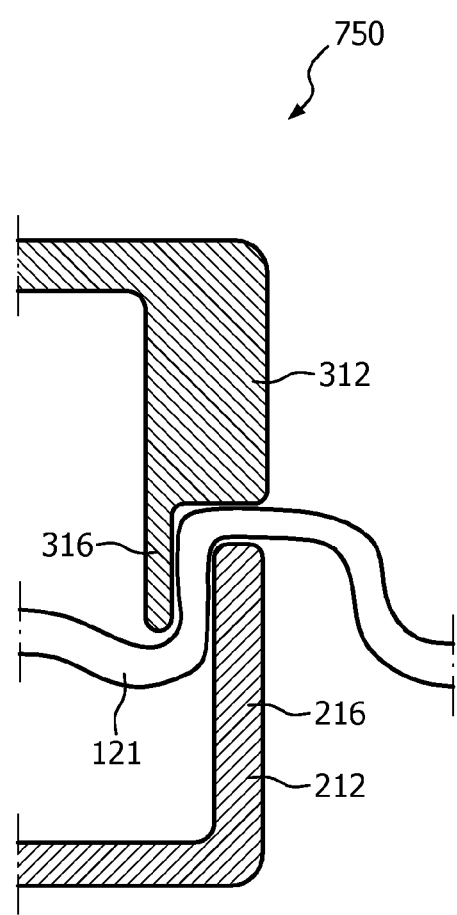
FIG. 6b illustrates the anti-pinch feature of the case seal.

Now referring to FIGS. 6a and 6b, a closure seal 750 between base 200 and lid 300 is described. In prior art carrying cases, protruding electrode wires could be damaged or severed when the lid was inadvertently forced shut against the case base. To minimize damage to wires in the unlikely event that carrying case 100 is inadvertently shut during use, a closure seal 750 is formed in the opposing exposed edges in base walls 212 and lid walls 312. A preferred embodiment of the closure seal 750 is shown in the section view FIG. 6b. Each lid wall 312 edge that faces a base wall 212 edge comprises a lid seal edge 316 that protrudes from and is offset from the exterior surface. A lid closure stop, not shown, causes a serpentine gap between base 200 and lid 300 when lid 300 is closed, through which a protruding electrode lead wire 121 can pass without damage. If additional protection from outside elements is desired, each of base seal edge 216 and lid seal edge 316 may be lined with a flexible elastomeric material which fills the gap when the lid is closed, but which allows electrode lead wire 121 to pass without damage.

Another embodiment of the present invention is a carrying case which incorporates features that enable testing of the internal contents. One such feature enables testing of the CPR Meter 140 during storage and prior to deployment so that the rescuer is confident that the CPR meter will provide accurate instruction during use. Another feature enables the physical testing of the portable defibrillator 110 buttons, which has never been contemplated in prior art carrying cases. Such a test can periodically confirm the proper mechanical operation of the defibrillator shock button.

Figure 9A:
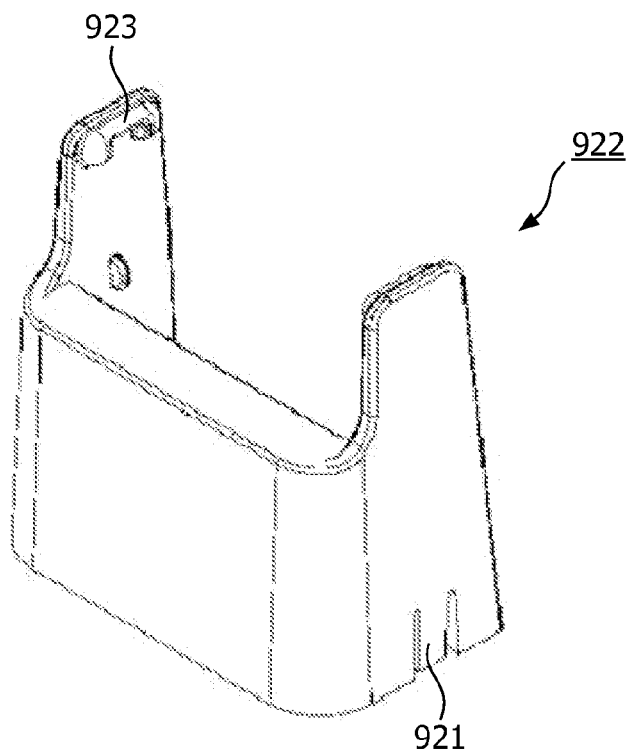
FIG. 9a illustrates a CPR meter storage bracket for holding a CPR meter inside the carrying case.

FIG. 9a is a more detailed illustration of the CPR meter storage bracket 922 shown in FIGS. 2a-c. Bracket 922 may be removably clipped into carrying case 100 with a CPR meter bracket base mount 921. CPR meter 140 is then clipped into CPR meter holding clip 923, which is offset upward from the bracket base such that the face of the CPR meter 140 is about coplanar with the face of the defibrillator 110 stored adjacent. Thus, both meter 140 and defibrillator 110 are immediately visible to the user. In addition, the space under the stored CPR meter 140 is available for storing other rescue items, such as a spare battery 112.

Figure 9B:
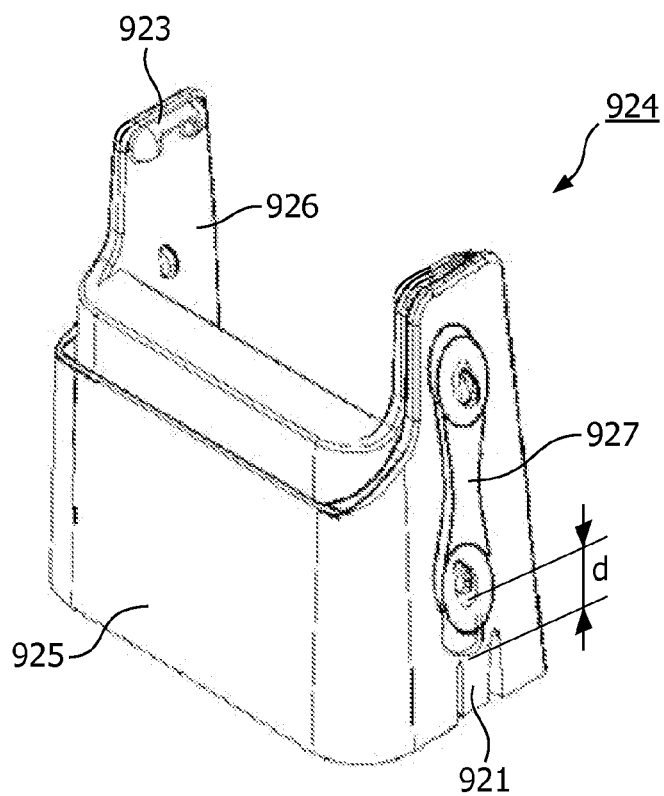
FIG. 9b illustrates an alternate embodiment of a CPR meter storage bracket, which comprises features to allow testing of a stored CPR meter.

Now referring to FIG. 9b, an alternate embodiment of CPR meter storage bracket 922 comprises a CPR meter test fixture 924. Like CPR meter storage bracket 922, CPR meter test fixture 924 is disposed to securely hold CPR meter 140 during storage. CPR meter test fixture 924 differs from the previously described CPR meter storage bracket 922, however, by comprising a test fixture base 925 and a vertically movable clip 926, connected with an internal spring means having a known spring constant, such as elastic band 927, coil spring, leaf spring, or underlying compressible material. Fixture base 925 is fixed to case bottom 200. CPR meter 140 is removably attached to movable clip 926 similar to that shown in FIG. 2.

CPR meter test fixture 924 with attached CPR meter 140 is disposed such that when lid 300 is closed, lid 300 compresses the CPR meter 140 and movable clip 926 by a known and fixed distance, shown as "d" in FIG. 9. The internal spring means thus generates a known counterforce on the CPR meter 140 force sensor as it is pressed against lid 300. An exemplary level of counterforce is about 4 kg, with a range of 2 kg-5 kg, with an exemplary fixed spring compression of 2 inches, with a range of between ¾ inch-3 inches.

Portable defibrillator 110, when it awakens for self-testing under its own internal periodic self-testing protocol, can be configured to also activate the attached CPR meter 140 and receive a signal corresponding to the sensed force. By comparing the sensed force with the known force, the defibrillator 110 can determine whether the CPR meter force sensor is operating properly and within calibration. If not, defibrillator 110 can generate a self-test failure alert.

With the carrying case lid 300 in the open position and the defibrillator 110 activated for self-testing, the CPR meter distance sensing can be tested by CPR meter test fixture 924 as well. In this embodiment, the difference in height between the CPR meter test fixture 924 in the uncompressed and fully compressed positions is also known. A user tests the CPR meter motion sensor by compressing the CPR meter 140 and movable clip 926 to the fully compressed position. Defibrillator 110 senses the CPR meter compression signal and compares it to the known distance. If the sensed and known distances differ in excess of an acceptable tolerance band, defibrillator 110 generates a self-test failure alert. Of course, defibrillator 110 can be configured to aurally and visually guide the user during the execution of this test.

Figure 10:
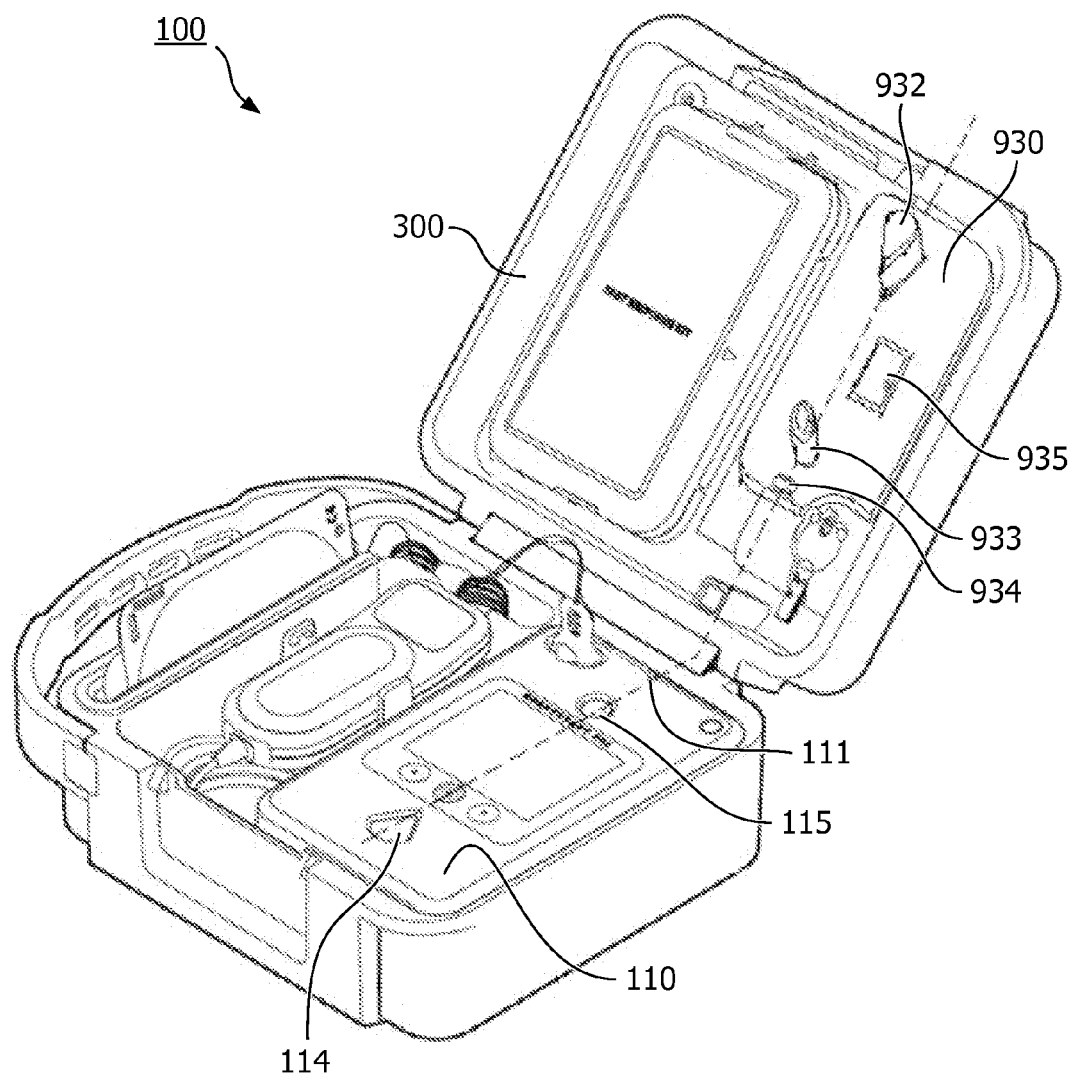
FIG. 10 illustrates one embodiment of a carrying case further comprising a defibrillator push button tester.

An optional defibrillator push button tester 930 may also be incorporated into carrying case lid 300. FIG. 10 illustrates one embodiment of the button tester 930, which comprises finger-like actuators 932, 933 extending from the bottom of an actuator case 934 mounted inside lid 300. Shock button actuator 932 is disposed such that its end is positioned over the defibrillator shock button 114 when the lid is shut. Similarly, on/off button actuator 933 is disposed such that its end is positioned over the defibrillator on/off button 115 when the lid is shut. Push button tester 930 also comprises a button tester sensor 934 to sense a periodic activation signal, issued from the underlying defibrillator when the defibrillator 110 awakes for a periodic self test. Button tester sensor 934 is preferably a light sensor or wireless sensor that senses a corresponding light or wireless signal that emanates from the defibrillator when it activates for self-testing. Push button tester 930 also comprises a button tester power supply 935 such as a replaceable battery with sufficient energy to operate periodically, preferably on a monthly basis, over an extended period of time.

Push button tester 930 is disposed to receive the periodic activation signal from defibrillator 110, such as by the flashing of ready status light 111, and subsequently extend actuators 932, 933 to press the respective underlying defibrillator push buttons. Defibrillator 110 senses the resulting operation of the push button, by sensing a change of continuity across the push button's electrical circuit, and passes the result to the self-test algorithm. If the defibrillator fails to sense an expected push button operation, it issues a self-test failure alert. Once the button self-test is complete, both defibrillator 110 and push button tester 930 revert to a standby mode of operation to save battery power.

Another embodiment of the defibrillator push button tester 930 requires no coordination with the self-test activation of the defibrillator 110. In this embodiment, the push button tester 930 actuates the actuator 932,933 on an independent schedule, and holds the actuator 932,933 down, i.e. button pressed, for a period of time long enough to overlap with a defibrillator self-test. The actuator 932,933 then releases for a second period of time long enough to overlap with the next defibrillator self-test. In this embodiment, the underlying defibrillator must only sense the change in button position from one self-test to the next to determine whether the button is operating properly.

Other variations within the scope of the aforedescribed invention will readily occur to those skilled in the art. For instance, the orientation of the latch could be reversed such that latch assembly 500 is pinned to base 200 instead of to lid 300. Other arrangements of the interior contents may be advantageous depending on the relative size and shape of the stowed components

What is claimed is:

1. A hinged carrying case for a portable defibrillator having an open position and a closed position comprising:
   a rigid base having a base interior region bounded by four base side walls and a bottom surface;
   a rigid lid having a lid interior region bounded by four lid side walls and a top surface;
   a hinge disposed on one base side wall connecting the base to the lid;
   a latch assembly disposed on a side of the carrying case opposite the hinge side wall for holding the lid to the base in the closed position;
   a handle with two ends, the handle disposed on a second side of the carrying case adjacent both of the hinge and the latch assembly;
   a defibrillator push button tester having an extensible defibrillator button actuator; and
   a plurality of interior compartments disposed in the base interior region and the lid interior region, wherein the portable defibrillator is located in the base interior region and the defibrillator push button tester is located in the lid interior region above and adjacent to the portable defibrillator when the carrying case is in the closed position, wherein the push button tester actuates the extensible button actuator against an underlying button adjacent defibrillator on a predetermined schedule.

2. The carrying case of claim 1 wherein the defibrillator push button tester further comprises a button tester sensor for sensing a self-test activation signal from the adjacent portable defibrillator.

3. The carrying case of claim 2 wherein the push button tester actuates the extensible button actuator against an underlying button in the adjacent defibrillator in response to the sensed self-test activation signal.

4. The carrying case of claim 2 wherein the button tester sensor is a light sensor.

5. The carrying case of claim 2 wherein the button tester sensor is a wireless sensor.

6. The carrying case of claim 1 further comprising a replaceable push button tester battery.

\* \* \* \* \*